United States Patent
Chiu et al.

(10) Patent No.: US 10,221,265 B2
(45) Date of Patent: Mar. 5, 2019

(54) METALLIC CROSSLINKING COAGENT, PREPARATION METHODS THEREOF, AND RESIN COMPOSITION COMPRISING THE SAME

(71) Applicant: KUO CHING CHEMICAL CO., LTD., Pingzhen, Taoyuan County (TW)

(72) Inventors: Kuan-Jung Chiu, Pingzhen (TW); Wen-Wei Cheng, Pingzhen (TW); Ting-Ti Huang, Pingzhen (TW); Chiu-Peng Tsou, Pingzhen (TW)

(73) Assignee: SUNKO INK CO., LTD., Taichung (TW)

( * ) Notice: Subject to any disclaimer, the term of this patent is extended or adjusted under 35 U.S.C. 154(b) by 279 days.

(21) Appl. No.: 15/051,342

(22) Filed: Feb. 23, 2016

(65) Prior Publication Data
US 2016/0326196 A1    Nov. 10, 2016

(30) Foreign Application Priority Data
May 7, 2015    (TW) .............................. 104114631 A

(51) Int. Cl.
| | |
|---|---|
| C08F 210/16 | (2006.01) |
| C07C 57/04 | (2006.01) |
| C08F 110/02 | (2006.01) |
| C07F 9/53 | (2006.01) |
| C07F 9/6571 | (2006.01) |
| C08L 9/00 | (2006.01) |
| C08L 21/00 | (2006.01) |
| C08F 210/18 | (2006.01) |

(52) U.S. Cl.
CPC ............ *C08F 210/16* (2013.01); *C07C 57/04* (2013.01); *C07F 9/5325* (2013.01); *C07F 9/657172* (2013.01); *C08F 110/02* (2013.01); *C08F 210/18* (2013.01); *C08L 9/00* (2013.01); *C08L 21/00* (2013.01)

(58) Field of Classification Search
None
See application file for complete search history.

(56) References Cited

FOREIGN PATENT DOCUMENTS

| JP | 56118441 | * | 2/1980 | .............. C08L 27/00 |
| JP | 2000273366 | * | 10/2000 | ............... C09D 5/16 |

OTHER PUBLICATIONS

Machine translation May 30, 2018 of JP56118441.*
Machine translation May 30, 2018 of JP2000273366.*

* cited by examiner

*Primary Examiner* — Clinton A Brooks
(74) *Attorney, Agent, or Firm* — Birch, Stewart, Kolasch & Birch, LLP

(57) ABSTRACT

Provided are a metallic crosslinking coagent, preparation methods thereof, and a resin composition comprising the metallic crosslinking coagent. With the active-hydrogen containing organic phosphorus compound group and metallophilic acrylate group, the metallic crosslinking coagent provides both stabilizer and flame-retardant effects, enhances the crosslinking efficiency of the resin composition, and improves the compatibility between flame retardant and the polymer. Accordingly, the metallic crosslinking coagent is effective to improve the mechanical properties of the application material and to develop a safe and environmentally friendly flame retardant material.

23 Claims, 3 Drawing Sheets

METALLIC CROSSLINKING COAGENT, PREPARATION METHODS THEREOF, AND RESIN COMPOSITION COMPRISING THE SAME

CROSS-REFERENCE TO RELATED APPLICATION

Pursuant to 35 U.S.C. § 119(a), this application claims the benefit of the priority to Taiwan Patent Application No. 104114631 filed May 7, 2015. The content of the prior application is incorporated herein by its entirety.

BACKGROUND OF THE INVENTION

1. Field of the Invention

The present invention relates to a novel metallic crosslinking coagent, particularly to a metallic crosslinking coagent for application to plastic material, preparation methods of the metallic crosslinking coagent, and a resin composition comprising the metallic crosslinking coagent.

2. Description of the Prior Arts

Nowadays, plastic materials are expected to provide good flame retardancy, mechanical property, thermal resistance, weather resistance, and safety to be widely used in various applications. To attain the flame retardancy, flame retardants, such as tetrabromobiphenyl A (TBBPA), polybrominated diphenylether (PBDE), polybrominated biphenyl (PBB), hexabromocyclododecane (HBCD), or polychloroalkane (for example, chlorinated paraffin (CP)), are typically added to the plastic materials to meet the flammability standards. However, due to safety concerns, the foresaid halogenated flame retardants are gradually prohibited or listed as controlled additives.

Researches are conducted to find a safer organic phosphorus flame retardant and inorganic flame retardant to replace the prohibited halogenated flame retardants. Nevertheless, organic phosphorus or inorganic flame retardants are usually incompatible and unstable in the low-polar rubber material, causing pollution, blooming or hydrolysis to the plastic product or mold made therefrom and thus deteriorating the physical properties of the plastic product.

To overcome the foregoing problems, an acrylate salt of metals represented by the following formula has been developed.

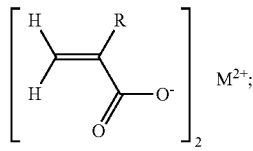

Wherein, $M^{2+}$ is divalent metal ion, and R is hydrogen (—H) or methyl group (—CH$_3$).

Common commercially available acrylate salts of metals include zinc diacrylate (ZDA), calcium diacrylate, zinc dimethacrylate (ZDMA), and fatty acid modified zinc diacrylate, their trade names include: Dymalink 633, Dymalink 634, Dymalink 705, and Dymalink 706 purchased from Cray Valley in France; K-CURE 339, K-CURE 439, K-CURE 633, and K-CURE 634 purchased from Kuo Ching Chemical Co., Ltd. in Taiwan; and ZN-DA 90 and ZN-DA 100 purchased from Nippon Shokubai Co. Ltd. The preparation methods and their applications are described in Taiwan Patent No. 530062, Japan Patent Application Publication No. S58-14416, Japan Patent Application Publication No. H4-10463, Japan Patent No. 4041175, Japan Patent No. 4286018, Japan Patent No. 4398157, U.S. Pat. No. 5,789,616, U.S. Pat. No. 6,278,010, and U.S. Pat. No. 7,217,829.

Said acrylate salts of metals can be used in a crosslinkable polymer composition and acts as a curing coagent. With the improvement of mechanical strength, stretching property, thermal resistance, wear resistance, solvent resistance, tensile strength, and adherence to metals, the acrylate salts of metals can be widely applied to the products of golf balls, rollers, sealing strips, cables, belts, and architectural materials.

As disclosed by Taiwan Patent No. 223652, Taiwan Patent No. 223095, European Patent Publication No. 0589701, Japan Patent Application Publication No. H2-158640, and Japan Patent Application Publication No. H6-256582, Sumitomo Chemical Co., Ltd. discloses a rubber composition for covering electric cables, which comprises (1) ethylene-α-olefin copolymer and/or ethylene-α-olefin-nonconjugated diene copolymer, (2) magnesium hydroxide and/or aluminum hydroxide, and (3) a zinc acrylate represented by the following formula:

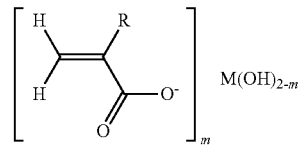

Wherein, M is a divalent metal ion, R is hydrogen or a methyl group, m ranges from 1 and 2. The zinc acrylate can be used in the composition to maintain the elasticity, anti-scorch property and workability of the covering electric cables.

Mitsubishi Rayon Co., Ltd. discloses a metal salt of acrylic acid and propanoic acid in Japan Patent Application Publication No. 2000273366, the metal salt of acrylic acid and propanoic acid are represented by the following formula:

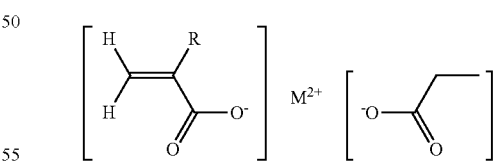

Wherein, $M^{2+}$ is a divalent metal ion, and R is hydrogen or a methyl group. As the chemical structure implies, the metal salt of acrylic acid and propanoic acid also contains no organic phosphorus oxide group, but their fields of application are totally different from the plastic industry.

Furthermore, Sankyo Organic Chemicals Co., Ltd. discloses oxaphosphaphenanthrene oxide derivative salts in Japan Patent Application Publication No. S56-118441, which have a chemical structure represented by the following formula:

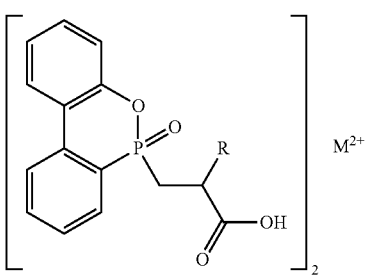

Wherein, $M^{2+}$ is a divalent metal ion, and R is hydrogen or a methyl group. As shown above, the disclosed organic phosphorus metal salts do not contain an unsaturated carbon-carbon double bond for crosslinking. Further, the publication merely mentions that the organic phosphorus metal salts can be added in polyvinyl chloride and act as a stabilizer, but the organic phosphorus metal salts are incapable of increasing the crosslinking efficiency of the polyvinyl chloride.

To overcome the shortcomings, the present invention provides a novel metallic crosslinking coagent to mitigate or obviate the aforementioned problems.

SUMMARY OF THE INVENTION

The objective of the present invention is to develop a novel metallic crosslinking coagent to act as both crosslinking coagent and flame retardant, and thus improves the applicability of a resin composition with the metallic crosslinking coagent.

To achieve the objective, the present invention provides a metallic crosslinking coagent having a chemical structure represented by the following formula (I):

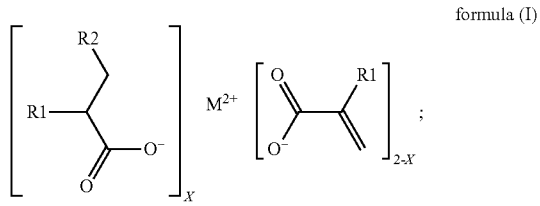

formula (I)

in the above formula (I),
$M^{2+}$ is a divalent metal ion;
R1 is hydrogen or an alkyl group;
R2 is

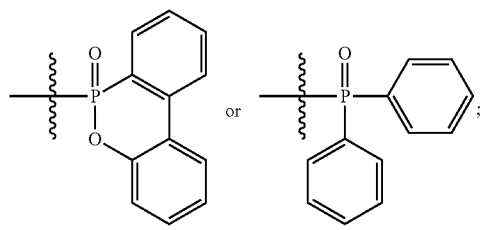 [SMILES: *P1(=O)Oc2ccccc2-c2ccccc21 ; *P(=O)(c1ccccc1)c1ccccc1]

and
X is larger than 0 and less than 2.

With the active-hydrogen contained in the organic phosphorus oxide group and the presence of metallophilic acrylate group, the novel metallic crosslinking coagent provides both stabilizer and flame-retardant properties when introducing in the resin composition. The metallic crosslinking coagent is further effective in improving the crosslinking efficiency of the resin composition and the mechanical properties of the material made from the resin composition.

Preferably, said $M^{2+}$ is zinc ion ($Zn^{2+}$), magnesium ion ($Mg^{2+}$), calcium ion ($Ca^{2+}$), or barium ion ($Ba^{2+}$). More preferably, said $M^{2+}$ is zinc ion ($Zn^{2+}$), magnesium ion ($Mg^{2+}$), or calcium ion ($Ca^{2+}$).

Preferably, X is larger than 0 and less than 1; and more preferably, X is larger than 0.1 and less than 0.9.

Preferably, the alkyl group is a saturated alkyl group having 1 to 6 carbon atom(s). More specifically, the alkyl group may be, but is not limited to, methyl group ($-CH_3$) or ethyl group ($-C_2H_5$).

The present invention provides a method of producing the foresaid metallic crosslinking coagent, comprising steps of:
reacting an unsaturated carboxylic acid and a divalent metal oxide in a nonpolar solvent to form a first mixture;
mixing an organic phosphorus compound and the first mixture to form a second mixture;
collecting the metallic crosslinking coagent from the second mixture by purification.

Preferably, the unsaturated carboxylic acid is reacted with the divalent metal oxide at a temperature ranging from 30° C. to 100° C., and the organic phosphorus compound is mixed with the first mixture at a temperature ranging from 30° C. to 100° C. More preferably, the unsaturated carboxylic acid is reacted with the divalent metal oxide at a temperature ranging from 40° C. to 80° C., and the organic phosphorus compound is mixed with the first mixture at a temperature ranging from 40° C. to 80° C.

According to the foresaid method, the applicable examples of the unsaturated carboxylic acid may be, but are not limited to, acrylic acid, methacrylic acid, 2-methylidenebutanoic acid, 2-methylidenepentanoic acid, 2-methylidenehexanoic acid, 2-methylideneheptanoic acid, and 2-methylideneoctanoic acid.

The applicable examples of the divalent metal oxide may be, but are not limited to, zinc oxide, magnesium oxide, calcium oxide, barium oxide, zinc hydroxide, magnesium hydroxide, calcium hydroxide, and barium hydroxide.

According to the foresaid method, the unsaturated carboxylic acid is reacted with the divalent metal oxide in a molar ratio ranging from 1.4:1 to 2.1:1, and the divalent metal oxide is reacted with the organic phosphorus compound in a molar ratio ranging from 1.0:0.05 to 1.0:2. Preferably, the molar ratio of the unsaturated carboxylic acid to the divalent metal oxide ranges from 1.85:1 to 2.05:1, and a molar ratio of the divalent metal oxide to the organic phosphorus compound ranges from 1.0:0.1 to 1.0:0.9.

According to the foresaid method, the nonpolar solvent is a hydrocarbon solvent having a boiling point within 50° C. to 150° C. under atmospheric pressure. The applicable examples of the hydrocarbon solvent may be, but are not limited to, benzene, toluene, xylene, cyclohexane, hexane, heptane, octane, and any combinations thereof.

Depending on the demands in different applications, the step "reacting an unsaturated carboxylic acid and a divalent metal oxide in a nonpolar solvent to form a first mixture" comprises: reacting the unsaturated carboxylic acid, the divalent metal oxide, and at least one additive in the nonpolar solvent to form the first mixture. The at least one additive comprises a surfactant, an antioxidant, a polymerization inhibitor or a lubricant.

Preferably, the method comprises: reacting the unsaturated carboxylic acid and the divalent metal oxide in the nonpolar solvent to form the first mixture; removing the remaining water from the first mixture to obtain a dehydrated first mixture; and mixing an organic phosphorus compound and the dehydrated first mixture to form the second mixture. The remaining water can be removed from the first mixture by distillation. The dehydration step is beneficial to increase the purity of the produced metallic crosslinking coagent.

The present invention provides another method of producing the foresaid metallic crosslinking coagent, comprising steps of:

reacting an unsaturated metal carboxylate and an organic phosphorus compound in a nonaqueous solvent to form a third mixture; and collecting the metallic crosslinking coagent from the third mixture by purification.

Preferably, the unsaturated metal carboxylate is reacted with the organic phosphorus compound at a temperature ranging from 30° C. to 100° C. More preferably, the unsaturated metal carboxylate is reacted with the organic phosphorus compound at a temperature ranging from 40° C. to 80° C.

According to said another method, the applicable examples of the unsaturated metal carboxylate may be, but are not limited to: zinc diacrylate, zinc dimethacrylate, zinc di(2-methylidenebutanoate), zinc di(2-methylidenepentanoate), zinc di(2-methylidenehexanoate), zinc di(2-methylideneheptanoate), zinc di(2-methylideneoctanoate), magnesium diacrylate, magnesium dimethacrylate, magnesium di(2-methylidenebutanoate), magnesium di(2-methylidenepentanoate), magnesium di(2-methylidenehexanoate), magnesium di(2-methylideneheptanoate), magnesium di(2-methylideneoctanoate), calcium diacrylate, calcium dimethacrylate, calcium di(2-methylidenebutanoate), calcium di(2-methylidenepentanoate), calcium di(2-methylidenehexanoate), calcium di(2-methylideneheptanoate), calcium di(2-methylideneoctanoate), barium diacrylate, barium dimethacrylate, barium di(2-methylidenebutanoate), barium di(2-methyl idenepentanoate), barium di(2-methylidenehexanoate), barium di(2-methylideneheptanoate), barium di(2-methylideneoctanoate), and any combinations thereof.

According to said another method, the unsaturated metal carboxylate is reacted with the organic phosphorus compound in a molar ratio ranging from 1:0.05 to 1:2. Preferably, the molar ratio of the unsaturated metal carboxylate to the organic phosphorus compound ranges from 1:0.1 to 1:0.9.

Depending on the demands in different applications, the step "reacting an unsaturated metal carboxylate and an organic phosphorus compound in a nonaqueous solvent to form a third mixture" comprises: mixing the unsaturated metal carboxylate, the organic phosphorus compound, and an additive in the nonaqueous solvent to form the third mixture, and the additive comprises a surfactant, an antioxidant, a polymerization inhibitor, or a lubricant.

According to said another method, the nonaqueous solvent is a hydrocarbon solvent having a water content less than 2% and a boiling point within 50° C. to 150° C. under atmospheric pressure. The applicable examples of the hydrocarbon solvent may be, but are not limited to, benzene, toluene, xylene, cyclohexane, hexane, heptane, octane, and any combinations thereof. Preferably, the water content of the nonaqueous solvent is less than 0.5%, and more preferably, ranges from 0.01% to 0.5%.

According to both of the foresaid methods, the applicable examples of the organic phosphorus compound are 9,10-dihydro-9-oxa-10-phosphaphenanthrene-10-oxide (DOPO) and diphenylphosphine oxide (DPPO).

According to both of the foresaid methods, various functional additives can be optionally used. For example, well-known surfactant, such as polyoxyethylene alkyl ether, sorbitan fatty acid ester, polyoxyethylene sorbitan fatty acid ester, silicon oil, sodium alkylbenzensulfonate, and sodium dioctyl sulfosuccinate, can be optionally added in the mixture to improve the dispersion. Well-known antioxidant, such as quinoline-based antioxidant, amine-based antioxidant, phenol-based antioxidant, sulfur-based antioxidant, also can be optionally added in the mixture for inhibiting or preventing the oxidation of the elastomers or the reaction induced by oxygen radicals. Specific examples of the antioxidants include, but are not limited to, N-phenyl-benzenamine reaction products with 2,4,4-trimethylpentene (CAS 68411-46-1), 2,6-di-tert-butyl-4-methyl-phenol, 2,2'-methylene-bis(6-tert-butyl-4-methylphenol), 4,6-bis(octylthiomethyl)-o-cresol. Well-known polymerization inhibitor, such as hydroquinone monomethylether, 2,6-di-tert-butyl-4-(dimethylaminomethyl) phenol, 2,2,6,6-tetramethylpiperidinooxy, also can be optionally used to delay scorch. Well-known lubricant, such as fatty acid, fatty acid metal salt, low molecular weight polyethylene, also can be used.

Further, the present invention also provides a resin composition comprising a polymer and the foresaid metallic crosslinking coagent. Said novel metallic crosslinking coagent is applied in the resin composition to offer both antioxidant and flame retardant properties, improving the crosslinking efficiency of the resin composition and the mechanical properties of the product made from the resin composition.

Preferably, the amount of the metallic crosslinking coagent ranges from 10 parts by weight to 900 parts by weight per 100 parts by weight of the polymer. More preferably, the amount of the metallic crosslinking coagent ranges from 200 parts by weight to 800 parts by weight per 100 parts by weight of the polymer.

Preferably, the resin composition comprises an organic peroxide, and the polymer is a vulcanizable polymer. Preferably, the amount of the metallic crosslinking coagent ranges from 5 parts by weight to 40 parts by weight and the amount of the organic peroxide ranges from 0.1 parts by weight to 3 parts by weight per 100 parts by weight of the polymer. More preferably, the amount of the metallic crosslinking coagent ranges from 15 parts by weight to 30 parts by weight and the amount of the organic peroxide ranges from 0.1 parts by weight to 2 parts by weight per 100 parts by weight of the polymer.

The applicable examples of the vulcanizable polymer may be, but are not limited to, polyolefin, ethylene-α-olefin copolymer, ethylene-α-olefin-nonconjugated diene copolymer, polyethylene (PE), ethylene propylene rubber (EP), ethylene propylene diene monomer rubber (EPDM), polybutene rubber (BR), polyisobutylene rubber (IIR), natural rubber (NR), polyisoprene rubber (IR), styrene-butadiene-styrene block copolymer (SBS), styrene-isoprene-styrene block copolymer (SIS), styrene butadiene rubber (SBR), partially-hydrogenated styrene-butadiene-styrene block copolymer, SBS-SEBS), nitrile rubber (NBR), polyolefin elastomer (POE), and any combinations thereof. Said polyethylene may be low-density polyethylene (LDPE), linear low-density polyethylene (LLDPE) or high-density polyethylene.

The organic peroxide includes, but is not limited to, alkyl hydroperoxides, dialkyl hydroperoxides, peroxyesters, diperoxyketals, diacyl peroxides, or peroxydicarbonates. More specifically, the applicable examples of the alkyl hydroperoxide may be, but are not limited to, tert-butyl-hydroperoxide, tert-amyl-hydroperoxide, and 2,5-dimethyl-hexane-2,5-dihydroperoxide. The applicable examples of the dialkyl hydroperoxide may be, but are not limited to, di-tert-butyl-hydroperoxide, di-tert-amyl-hydroperoxide, 2,5-bis(tert-butylperoxy)-2,5-dimethylhexane, and 2,5-dimethyl-2,5-di(tert-butylperoxy)-hexyne-3. The applicable examples of the peroxyeser may be, but are not limited to, tert-butyl peroxybenzoate, tert-amyl peroxybenzoate, tert-butyl peroxyacetate, tert-butyl monoperoxymaleate, tert-butyl peoxypivalate, tert-butyl peroxyneodecanoate, tert-amyl peroxyneodecanoate, tert-butyl peroxy-2-ethylhexanoate, tert-butyl peroxyisobutyrate, tert-butyl peroxyneoheptanoate, tert-butyl peroxy-3,5,5-trimethyl-hexanoate, tert-butyl peroxy-2-ethylhexyl carbonate, tert-amyl peroxy-2-ethylhexyl carbonate, and 2,5-dimethyl-2,5-di(2-ethylhexanoylperoxy)hexane. The applicable examples of the diperoxyketal may be, but are not limited to, 3,6,9-triethyl-3,6,9-trimethyl-1,4,7-triperoxonane, 1,1-bis(tert-butylperoxy)-3,3,5-trimethylcyclohexane, 1,1-bis(tert-butylperoxy) cyclohexane, and 2,2-di (tert-butylperoxy)butane). The applicable examples of the diacyl peroxide may be, but are not limited to, benzoyl peroxide, bis(3,5,5-trimethyl-1-oxohexyl)peroxide, and dilauroyl peroxide. The applicable examples of the peroxydicarbonate may be, but are not limited to, bis(2-ethylhexyl)peroxydicarbonate, bis(4-tert-butyl-cyclohexyl)peroxydicarbonate, dimyrityl peroxyldicarbonate, and dicetyl peroxyducarbonate.

Preferably, the resin composition comprises a halogen-free flame retardant, which can be added in the resin composition as required to retard flame or suppress smoke. The halogen-free flame retardant may be an organic phosphorus-based flame retardant, an inorganic flame retardant, or their combination. With use of the metallic crosslinking coagent, the compatibility between the polymer and the organic phosphorus-based or inorganic flame retardant is improved, and the resin composition is capable of being vulcanized. Accordingly, the resin composition comprising the metallic crosslinking coagent becomes a safer and environmentally friendly flame-retardant material compared to the conventional resin composition.

The applicable organic phosphorus-based flame retardant may be, but is not limited to, phosphorus-containing organic compounds, phosphorus and nitrogen-containing organic compounds, or their combination. More specifically, the phosphorus-containing organic compounds may be, but is not limited to, triphenyl phosphate (TPP), cresyl diphenyl phosphate (CDP), triisopropylphenyl phosphate (IPPP, for example, commercially available Reofos 95), bisphenol-A bis(diphenyl phosphate) (BDP), hydroquinone bis-(diphenyl phosphate), resorcinol bis-(diphenyl phosphate) (RDP), resorcinol dixylenylphosphate (RDXP, for example, commercially available PX-200), 9,10-dihydro-9-oxa-10-phosphaphenanthrene-10-oxide (DOPO), 2-(6-oxido-6H-dibenz[c,e][1,2]oxaphophorin-6-yl)-1,4-benzenediol (DOPO-HQ), or 2-((6-oxido-6H-dibenz[c,e][1,2]oxaphophorin-6-yl)-methyl)-butanedioic acid (DOPO-ITA). The phosphorus and nitrogen-containing organic compound may be, but is not limited to, ammonium polyphosphate, melamine phosphate, or phosphazene such as commercially available SPS-100, SPB-100, SPH-100, SPC-100 manufactured by Otsuka Chemical Co., Ltd.

The applicable inorganic flame retardant includes metal hydroxide, metal oxide, metal salts, and any combinations thereof. The applicable examples of the inorganic flame retardant may be, but are not limited to, magnesium hydroxide ($Mg(OH)_2$), aluminum hydroxide ($Al(OH)_3$), antimony oxide ($Sb_2O_3$), molybdenum oxide ($MoO_3$), zinc borate, magnesium carbonate, aluminum diethylphosphinate such as commercially available Exolit OP-935 manufactured by Clariant, or Sn—Zn compound such as commercially available Flamtard H or Flamtard S manufactured by Nippon Light Metal Co., Ltd.

In accordance with the present invention, the amount of the metallic crosslinking coagent ranges from 1 part by weight to 50 parts by weight, and a total amount of the halogen-free flame retardant, i.e., a total amount of the organic phosphorus-based flame retardant and the inorganic flame retardant, ranges from 10 parts by weight to 200 parts by weight per 100 parts by weight of the polymer. Preferably, the amount of the metallic crosslinking coagent ranges from 5 parts by weight to 40 parts by weight, and the total amount of the halogen-free flame retardant ranges from 20 parts by weight to 150 parts by weight per 100 parts by weight of the polymer. More preferably, the amount of the metallic crosslinking coagent ranges from 15 parts by weight to 30 parts by weight, and the total amount of the halogen-free flame retardant ranges from 30 parts by weight to 100 parts by weight per 100 parts by weight of the polymer.

When adopting the organic phosphorus-based flame retardant only, the amount of the metallic crosslinking coagent ranges from 1 part by weight to 50 parts and an amount of the organic phosphorus-containing flame retardant ranges from 10 parts by weight to 40 parts by weight per 100 parts by weight of the polymer. Preferably, the amount of the metallic crosslinking coagent ranges from 15 parts by weight to 30 parts by weight and the amount of the organic phosphorus-containing flame retardant ranges from 20 parts by weight to 30 parts by weight per 100 parts by weight of the polymer. In comparison with the conventional acrylate salts of metals, the novel metallic crosslinking coagent of the present invention improves the compatibility between the resin composition and the organic phosphorus-based flame retardant, thus allowing to increase the amount of the organic phosphorus-based flame retardant added in the resin composition.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
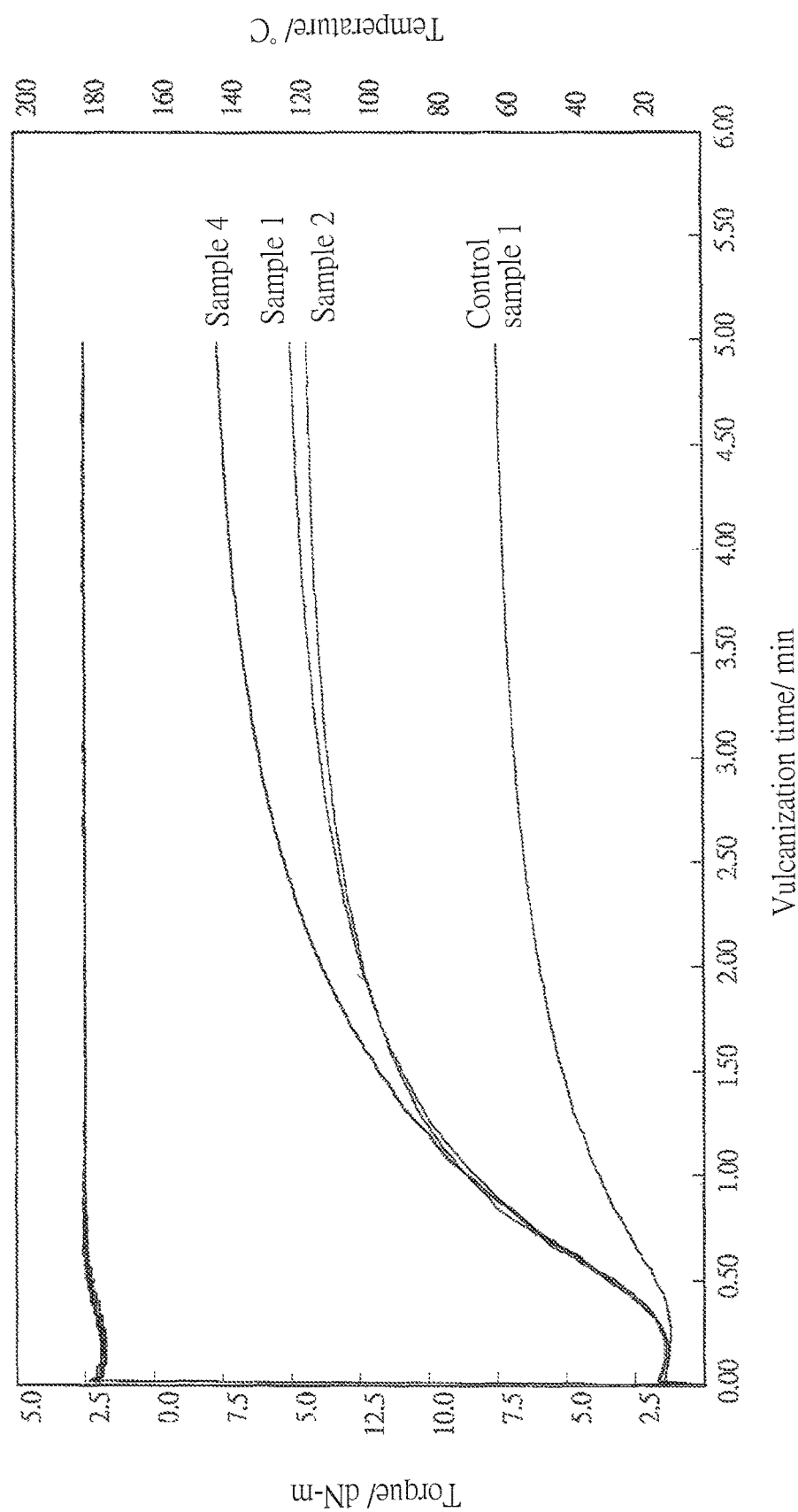
FIG. 1 is a graph showing the vulcanization curves of the resin composition comprising the metallic crosslinking coagent of Example 1 (Sample 1), of the resin composition comprising the metallic crosslinking coagent of Example 5 (Sample 2), of the resin composition comprising the commercial zinc diacrylate of Comparative Example 1 (Sample 4), and of the resin composition without adding any metallic crosslinking coagent (Control Sample 1).

Hereinafter, one skilled in the arts can easily realize the advantages and effects of the present invention from the following examples. Therefore, it should be understood that the descriptions proposed herein are just preferable examples for the purpose of illustrations only, not intended to limit the scope of the invention. Various modifications and variations could be made in order to practice or apply the present invention without departing from the spirit and scope of the invention.

The physical and chemical properties of the metallic crosslinking coagent were analyzed by proton nuclear magnetic resonance spectroscopy ($^1$H-NMR), $^{31}$P nuclear magnetic resonance spectroscopy ($^{31}$P-NMR), Fourier transform infrared spectroscopy (FTIR), and ash to determine the chemical structure of the metallic crosslinking coagent. The percentage of the effective amounts of acrylate and of methacrylate were determined by redox titration and represented by [AA] % and [MAA] % as below. The physical and chemical properties were determined by the method described as follows.

1. Yield

The theoretical mass of the metallic crosslinking coagents was determined based on the respective metal oxide or metal hydroxide as limiting reagent. The actual mass of the purified and dried product was divided by the theoretical mass and then multiplied by 100% to find the yield (unit: %).

2. Phosphorus Content

Each of the phosphorus content was calculated by multiplying the equivalent of phosphorus (x) contained in the metallic crosslinking coagent by the atomic weight of phosphorus, about 30.97, and then dividing by the molecular weight of the respective metallic crosslinking coagent.

3. Melting Point

The melting point analyses were carried out with a BUCHI melting point instrument B-540. Each sample was placed into a capillary tube for melting point analysis around 1 centimeter in height. During the experiments, the samples were heated rapidly up to 40° C. for a steady state, and then heated with a heating rate of 2° C. per minute to observe and record the temperatures while the sample started melting and fully melted.

4. FTIR

Each sample was mixed with potassium bromide, KBr, in a weight ratio of 1:50 to 1:100 and then pressed after fully grinding to prepare the pressed sample. The FTIR spectra were obtained with a Thermo Nicolet 330FT-IR spectrometer within the range 4000 cm$^{-1}$ to 450 cm$^{-1}$ to determine the characteristics of the functional groups of the metal crosslinking coagent.

5. $^1$H-NMR $^1$H-NMR spectra were recorded on a Varian NMR-400 spectrometer at 400 MHz. Each sample was dispersed in deuterated chloroform, CDCl$_3$, and then added with a trace of deuterated dimethyl sulfoxide, d$_6$-DMSO for analyses. Data were reported as chemical shift (multiplicity, coupling constant). The chemical shifts, symbolized by δ, were reported in ppm, and the coupling constants, symbolized by J, were reported in hertz (Hz). Regarding multiplicity, "s" represented singlet, "d" represented doublet, "t" represented triplet, "dd" represented doublet of doublets, "td" represented triplet of doublets, "m" represented multiplet, and "br." represented a broad band.

6. $^{31}$P-NMR $^{31}$P-NMR spectra were recorded on a Varian Unityinova 500 spectrometer at 202 MHz. Each sample was also dispersed in CDCl$_3$, and then added with a trace of d$_6$-DMSO for test. Data were reported as the description similar with $^1$H-NMR.

7. Ash 1 gram of precisely weighed sample, as initial weight W0, was placed in the furnace and heated to 600±25° C. for 3 hours to observe the color of the sample. The sample was placed back into the furnace and heated to 800±25° C. for 2 hours until whitish-grey ash was obtained. The whitish-grey ash was moved into the cabinet drier and cooled down to room temperature, and then weighed and recorded its residue weight W1.

The analyzed ash content was calculated by the calculation:

$$[(W1 - W0)/W0] \times 100\%.$$

The calculated ash content was calculated by the calculation:

$$\frac{\text{the molecular weight of the metal oxide} * 1}{\text{theoretical molecular weight of the product}} \times 100\%.$$

8. [AA] % or [MAA] %

0.1 grams of precisely weighed sample, reading to four-decimal place precision, in a 250 ml triangular flask was added with 20 ml of glacial acetic acid, 20 ml of 0.1 N bromine agent, 3 ml of concentrated hydrochloric acid (32 wt %) in order in a 30° C. to 40° C. water bath for one hour. Then 50 ml of deionized water and 15 ml of potassium iodide reagent were added in the mixture, and then the flask was fully shaken and set for 10 minutes. After that, the mixture was titrated with 0.1 N standard solution of sodium thiosulfate until the solution changed into light yellow. 1 ml of starch indicator was added, and the titration was continued until the solution became colorless and the volume of the standard solution of sodium thiosulfate used (Vs) was recorded. The aforementioned steps were repeated without adding any sample, and then the volume of the standard solution of sodium thiosulfate used (Vo) was recorded.

Said 0.1 N of bromine agent was obtained by diluting the mixture of 2.8 grams of potassium bromate and 15 grams of bromide with water to 1 liter, and said potassium iodide reagent was obtained by dissolving the 6.5 grams of potassium iodide in 100 ml of deionized water.

The percentage of effective amounts of the acrylate, abbreviated as [AA] %, by titration and calculation and the percentage of effective amounts of the methacrylate, abbreviated as [MAA] %, by titration and calculation were calculated as follows:

[AA] % by titration=[0.1 N*(Vo−Vs)*(72/2)]/0.1× 100%.

[MAA] % by titration=[0.1 N*(Vo−Vs)*(86/2)]/0.1× 100%.

[AA] % by calculation=[72*(2−X)/molecular weight of the product]×100%.

[MAA] % by calculation=[86*(2−X)/molecular weight of the product]×100%.

Example 1

A 500 ml four-necked cylindrical shaped reaction flask equipped with a mechanical stirrer, a thermometer, a dropping funnel, and a Dean-Stark trap was charged with toluene (177 grams) and zinc oxide (45.00 grams, 0.553 moles), then slowly added with acrylic acid (81.64 grams, 1.133 moles) through the dropping funnel while heated to 50±5° C. and stirred at the temperature for 2 hours to obtain the first mixture. The used acrylic acid was purchased from Formosa Plastics Corporation and contained 200±20 ppm of hydroquinone monomethylether.

The first mixture was subjected to vacuum distillation to remove about 9.95 grams of water therefrom, and was added with 9,10-dihydro-9-oxa-10-phosphaphenanthrene-10-oxide (about 35.2 grams, 0.163 moles) after back to normal pressure and stirred for 1 hour to obtain a second mixture.

The second mixture was subjected to vacuum distillation to recycle toluene therefrom and then dried and crumbled to give 143.8 grams of white powders (theoretical mass: 149.7 grams, yield: 96.1%), which contained 3.37% of phosphorus and remained unmelted at 220° C., i.e., had a melting point more than 220° C. Data of $^1$H-NMR spectrum (400 MHz, CDCl$_3$+d$_6$DMSO): δ7.85-7.73 (m), 7.57 (t, J=7.8 Hz), 7.36 (m), 7.26-7.22 (m), 7.12 (t, J=5.6 Hz), 7.07 (d, J=7.6 Hz), 6.18 (d, J=17.2 Hz), 6.00 (dd, J=20.8 Hz, J=10.2 Hz), 5.58 (d, J=10 Hz), 2.46-2.41 (m), 2.24-2.16 (m). Data of $^{31}$P-NMR spectrum (202 MHz, CDCl$_3$+d$_6$DMSO): δ41.05, 39.56, 21.51, 8.71. Data of FTIR spectrum: λ3400 (br.), 1644, 1548, 1442, 1372, 1276, 1198, 1140, 1094, 1058, 1038, 986, 935, 831, 760, 676, 598, 552 cm$^{-1}$. The analyzed and calculated ash contents were 37.2% and 30.0%, and [AA] % by titration and calculation were 50.7% and 45.3%.

The chemical structure of the white powders could be determined by the results of the foresaid analyses as follows:

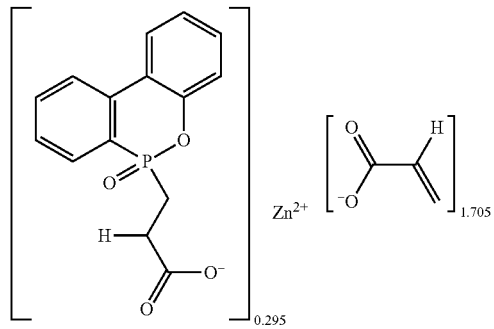

Example 2

The metallic crosslinking coagent of Example 2 was mainly prepared by the method as described in Example 1, except that the first mixture was subjected to vacuum distillation to remove water and added with 9,10-dihydro-9-oxa-10-phosphaphenanthrene-10-oxide (99.2 grams, 0.459 moles) after back to normal pressure and stirred for 1 hour to obtain a second mixture.

The second mixture was subjected to vacuum and then dried and crumbled to give 202.5 grams of white powders (theoretical mass: 214.0 grams, yield: 94.6%), which contained 6.64% of phosphorus and had a melting point about 72° C. to 157° C. Data of $^1$H-NMR spectrum (400 MHz, CDCl$_3$+d$_6$DMSO): δ7.86-7.75 (m), 7.59 (t, J=7.4 Hz), 7.39 (m), 7.28-7.21 (m), 7.16-7.05 (m), 6.23 (d, J=17.2 Hz), 5.99 (dd, J=16.8 Hz, J=10.6 Hz), 5.65 (d, J=9.6 Hz), 2.48-2.45 (br.), 2.24 (br.) Data of $^{31}$P-NMR spectrum (202 MHz, CDCl$_3$+d$_6$DMSO): δ39.34, 38.26, 19.65, 6.41. Data of FTIR spectrum: λ3240 (br.), 1721, 1643, 1563, 1440, 1371, 1322, 1276, 1140, 1093, 1055, 1037, 1003, 986, 831, 758, 679, 617, 599, 530 cm$^{-1}$. The analyzed and calculated ash contents were 34.7% and 21.0%, and [AA] % by titration and calculation were 42.4% and 21.8%.

The chemical structure of the white powders could be determined by the results of the foresaid analyses as follows:

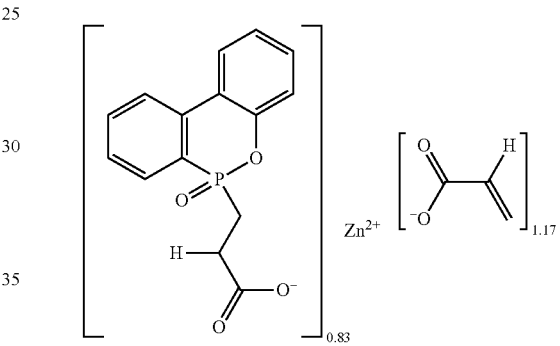

Example 3

The metallic crosslinking coagent of Example 3 was mainly prepared by the method as described in Example 1, except that the added divalent metal oxide of the instant Example was magnesium oxide (45.00 grams, 1.117 moles), the amount of acrylic acid of the instant Example was 164.8 grams (2.287 moles), and the amount of 9,10-dihydro-9-oxa-10-phosphaphenanthrene-10-oxide of the instant Example was 56.6 grams (0.262 moles).

After drying and crumbling steps, 230.1 grams (theoretical mass: 246.9 grams, yield: 93.2%) of white powders were obtained, which contained 3.34% of phosphorus and had a melting point about 139.4° C. to 182° C. Data of $^1$H-NMR spectrum (400 MHz, CDCl$_3$+d$_6$DMSO): δ7.80 (m), 7.14-6.74 (m), 6.12 (m), 5.98 (m), 5.54 (m), 2.22 (br. s), 2.04 (br. s). Data of $^{31}$P-NMR spectrum (202 MHz, CDCl$_3$+d$_6$DMSO): δ 40.58, 13.17 (br.). Data of FTIR spectrum: λ3400 (br.), 1686, 1644, 1558, 1434, 1364, 1321, 1276, 1188, 1141, 1114, 1097, 1056, 1021, 987, 962, 837, 759, 679, 575, 489 cm$^{-1}$. The analyzed and calculated ash contents were 25.3% and 18.6%, and [AA] % by titration and calculation were 69.2% and 58.6%.

The chemical structure of the white powders could be determined by the results of the foresaid analyses as follows:

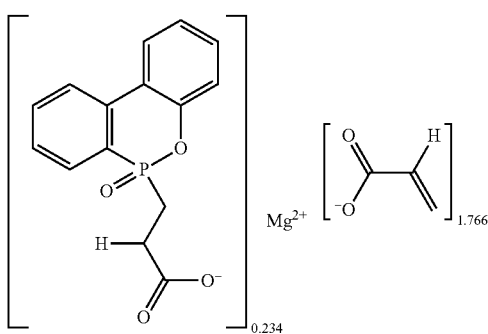

Example 4

The metallic crosslinking coagent of Example 4 was mainly prepared by the method as described in Example 1, except that the acrylic acid of Example 1 was replaced by the methacrylic acid, the amount of methacrylic acid was 97.0 grams (1.13 moles), the amount of 9,10-dihydro-9-oxa-10-phosphaphenanthrene-10-oxide was 71.1 grams (0.329 moles). Said methacrylic acid was purchased from Formosa Plastics Corporation and contained 250±20 ppm of hydroquinone monomethylether.

After drying and crumbling steps, 196.75 grams (theoretical mass: 201.4 grams, yield: 97.7%) of white powders were obtained, which contained 5.06% of phosphorus and remained unmelted at 220° C. Data of $^1$H-NMR spectrum (400 MHz, CDCl$_3$+d$_6$DMSO): δ7.76 (t, J=7.2 Hz), 7.52 (t, J=6 Hz), 7.31 (m), 7.20 (t, J=7.2 Hz), 7.11-6.99 (m), 5.92 (s), 5.30 (s), 2.78-2.45 (m), 2.01-1.85 (m), 1.74 (s), 1.14 (dd, J=18.4 Hz, J=6.6 Hz). Data of $^{31}$P-NMR spectrum (202 MHz, CDCl$_3$+d$_6$DMSO): δ 38.46, 38.03, 20.33, 7.05. Data of FTIR spectrum: λ3230 (br.), 2977, 1712, 1608, 1422, 1372, 1278, 1201, 1145, 1118, 1060, 937, 831, 756, 617 cm$^{-1}$. The analyzed and calculated ash contents were 32.4% and 22.3%, and [MAA] % by titration and calculation were 27.2% and 33.2%.

The chemical structure of the white powders could be determined by the results of the foresaid analyses as follows:

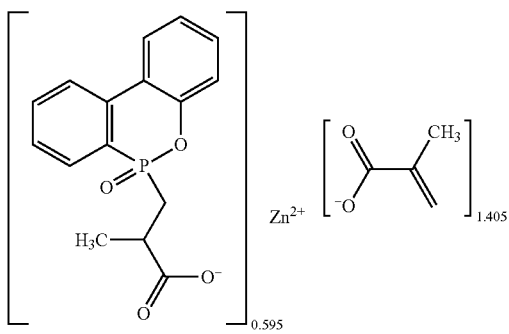

Example 5

The metallic crosslinking coagent was mainly prepared by the method as described in Example 1, except that the 9,10-dihydro-9-oxa-10-phosphaphenanthrene-10-oxide of Example 1 was replaced by the diphenylphosphine oxide in an amount of 35.19 grams (0.174 moles).

After drying and crumbling steps, 148.7 grams (theoretical mass: 150.0 grams, yield: 99.1%) of white powders were obtained, which contained 3.6% of phosphorus and had a melting point about 94.6° C. to 200° C. Data of $^1$H-NMR spectrum (400 MHz, CDCl$_3$+d$_6$DMSO): δ7.59 (d, J=6.8 Hz), 7.56 (d, J=7.2 Hz), 7.39 (td, J=7.4 Hz, J=1.2 Hz), 7.30 (td, J=7.4 Hz, J=2.4 Hz), 6.12 (dd, J=17.2 Hz, J=2 Hz), 5.98 (dd, J=17.2 Hz, J=10 Hz), 5.52 (dd, J=10 Hz, J=1.6 Hz), δ2.57 (t, J=8.3 Hz), 2.43 (t, J=6.5 Hz). Data of $^{31}$P-NMR spectrum (202 MHz, CDCl$_3$+d$_6$DMSO): δ40.59, 28.17. Data of FTIR spectrum: λ3400 (br.), 1644, 1547, 1439, 1371, 1275, 1161, 1123, 1069, 987, 830, 743, 726, 694, 536 cm$^{-1}$. The analyzed and calculated ash contents were 37.1% and 30.0%, and [AA] % by titration and calculation were 41.4% and 44.8%.

The chemical structure of the white powders could be determined by the results of the foresaid analyses as follows:

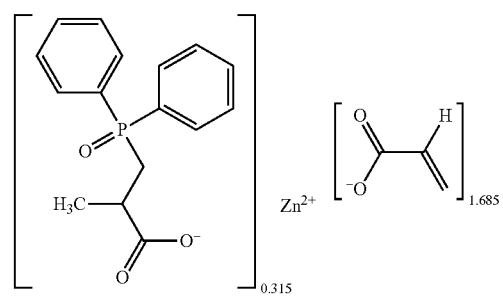

Example 6

A 500 ml four-necked cylindrical shaped reaction flask equipped with a mechanical stirrer, a thermometer, and distillation apparatus was placed with 180 grams of toluene, 120 grams of K-CURE339 (contained 92 wt % of zinc diacrylate and 8 wt % of zinc stearate, i.e., the amount of the zinc diacrylate was 0.532 moles), and 35.19 grams (0.174 moles) of diphenylphosphine oxide. The solution was then heated to 60±5° C. and stirred at the temperature for 1 hour to obtain a third mixture.

The third mixture was then vacuum distilled to recycle toluene and dried until no mass variation was noted. 149.61 grams (theoretical mass: 155.19 grams, yield: 96.4%) of white powders were obtained after crumbling. Said white powders contained 3.47% of phosphorus and had a melting point about 93.1° C. to 210° C. Data of $^1$H-NMR spectrum (400 MHz, CDCl$_3$+d$_6$DMSO): δ7.58 (d, J=7.2 Hz), 7.55 (d, J=7.6 Hz), 7.38 (t, J=7 Hz), 7.29 (td, J=8 Hz, J=2.8 Hz), 6.12 (dd, J=17.2 Hz, J=0.8 Hz), 5.97 (dd, J=17.2 Hz, J=10 Hz), 5.52 (dd, J=10 Hz, J=1.6 Hz), 2.53 (t, J=8.4 Hz), 2.41 (t, J=5.95 Hz), 2.11 (t, J=7.6 Hz), 1.40 (q, J=7 Hz), 1.15-1.07 (m), 0.71 (t, J=6.8 Hz). Data of $^{31}$P-NMR spectrum (202 MHz, CDCl$_3$+d$_6$DMSO): δ40.90, 28.40. FTIR spectrum: λ3400 (br.), 2917, 2848, 1644, 1568, 1438, 1368, 1274, 1161, 1123, 1099, 1067, 987, 900, 831, 743, 725, 694, 593, 536 cm$^{-1}$. The analyzed and calculated ash contents were 25.1% and 29.1%, and [AA] % by titration and calculation were 38.1% and 43.3%.

The chemical structure of the white powders could be determined by the results of the foresaid analyses as follows:

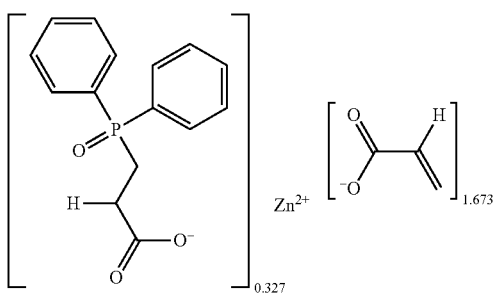

Example 7

The metallic crosslinking coagent of Example 7 was mainly prepared by the method as described in Example 1, except that the acrylic acid of Example 1 was replaced by the methacrylic acid, the amount of methacrylic acid was 97.0 grams (1.13 moles), and the amount of 9,10-dihydro-9-oxa-10-phosphaphenanthrene-10-oxide was 39.44 grams (0.182 moles). Said methacrylic acid was purchased from Formosa Plastics Corporation and contained 250±20 ppm of hydroquinone monomethylether.

After drying and crumbling steps, 161.4 grams (theoretical mass: 164.0 grams, yield: 98.4%) of white powders were obtained, which contained 3.32% of phosphorus and had a melting point about 146.2° C. to 250° C. Data of $^1$H-NMR spectrum (400 MHz, CDCl$_3$+d$_6$DMSO): δ7.87-7.77 (m), 7.55 (d, J=5.6 Hz), 67.33 (t, J=8 Hz), 7.20 (d, J=8.4 Hz), 7.13-6.96 (m), 5.95 (s), 5.33 (s), 2.82-2.46 (m), 62.03-1.87 (m), 1.78 (s), 1.16 (d, d, J=18.4 Hz, J=7.2 Hz). Data of $^{31}$P-NMR spectrum (202 MHz, CDCl$_3$+d$_6$DMSO): δ39.20, 20.63, 7.99. FTIR spectrum: λ3350 (br.), 2979, 1651, 1607, 1549, 1423, 1373, 1288, 1246, 1147, 1110, 1052, 1039, 1010, 978, 943, 831, 753, 622, 555, 439 cm$^{-1}$. The analyzed and calculated ash contents were 23.4% and 26.5%, and [MAA] % by titration and calculation were 63.6% and 46.9%.

The chemical structure of the white powders could be determined by the results of the foresaid analyses as follows:

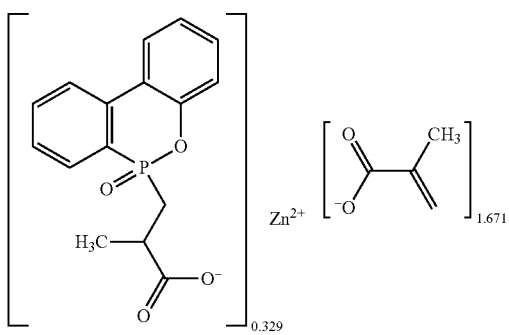

Example 8

The metallic crosslinking coagent of Example 8 was mainly prepared by the method as described in Example 1, except that the amount of 9,10-dihydro-9-oxa-10-phosphaphenanthrene-10-oxide was increased to 153.99 grams (0.712 moles).

After drying and crumbling steps, 260.3 grams (theoretical mass: 268.7 grams, yield: 96.9%) of white powders were obtained, which contained 8.23% of phosphorus and had a melting point about 62° C. to 150° C. Data of $^1$H-NMR spectrum (400 MHz, CDCl$_3$+d$_6$DMSO): δ7.82-7.67 (m), 7.54 (t, J=7.6 Hz), 7.32 (m), 7.23-7.19 (m), 7.13-7.03 (m), 6.13 (d, 5.95 (d, d, J=17 Hz, J=10.8 Hz), 5.54 (d, J=10 Hz), 2.45-2.37 (m), 2.28-2.20 (m). Data of $^{31}$P-NMR spectrum (202 MHz, CDCl$_3$+d$_6$DMSO): δ40.67, 39.40, 20.84, 7.63. FTIR spectrum: λ1722.8, 1643.6, 1594.6, 1478, 1433, 1371, 1320, 1276, 1197, 1145, 1119, 1097, 1057, 1042, 985, 921, 831, 757, 696, 680, 616, 598, 530 cm$^{-1}$. The analyzed and calculated ash contents were 33.3% and 16.7%, and [AA] % by titration and calculation were 29.8% and 10.6%.

The chemical structure of the white powders could be determined by the results of the foresaid analyses as follows:

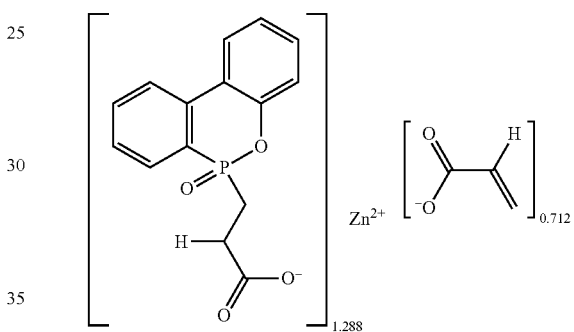

Example 9

A 500 ml four-necked cylindrical shaped reaction flask equipped with a mechanical stirrer, a thermometer, and distillation apparatus was charged with toluene (180 grams), zinc diacrylate (115 grams, 0.555 moles) and 9,10-dihydro-9-oxa-10-phosphaphenanthrene-10-oxide (35.0 grams, 0.162 moles), and then heated to 65° C. to 75° C. under stirring for 1 hour to form a third mixture.

The third mixture was then vacuum distilled to recycle toluene and dried until no mass variation was noted. 145.6 grams (theoretical mass: 150 grams, yield: 97.1%) of white powders were obtained after crumbling. Said white powders contained 3.34% of phosphorus and remained unmelted at 220° C. Data of $^1$H-NMR spectrum (400 MHz, CDCl$_3$+d$_6$DMSO): δ7.81-7.74 (m), 7.53 (t, J=7.8 Hz), 7.32 (m), 7.24-7.19 (m), 7.10 (t, J=5.6 Hz), 7.04 (d, J=7.6 Hz), 6.12 (d, J=16.8 Hz), 5.95 (dd, J=18.2 Hz, J=10 Hz), 5.52 (d, J=10 Hz), 2.44-2.40 (m), 2.17 (m). Data of FTIR spectrum: λ3396 (br.), 1643, 1559, 1437, 1368, 1275, 1139, 1059, 985, 831, 760, 671, 617, 527 cm$^{-1}$. The analyzed and calculated ash contents were 36.4% and 30.0%, and [AA] % by titration and calculation were 49.6% and 45.3%.

The chemical structure of the white powders could be determined by the results of the foresaid analyses as follows:

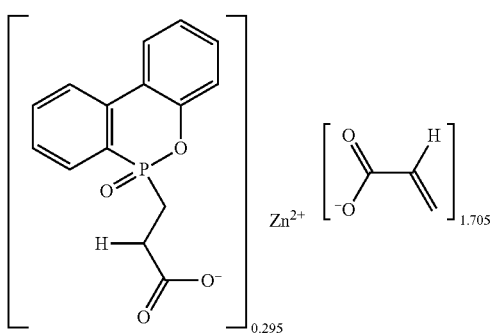

Example 10

A 500 ml four-necked cylindrical shaped reaction flask equipped with a mechanical stirrer, a thermometer, and distillation apparatus was charged with toluene (177 grams), calcium oxide (42.13 grams, 0.753 moles), then slowly added with acrylic acid (111.12 grams, 1.543 moles) through the dropping funnel while heated to 50±5° C. and stirred at the temperature for 2 hours to obtain the first mixture.

The first mixture was subjected to vacuum distillation to remove about 13.55 grams of water therefrom, and was added with 9,10-dihydro-9-oxa-10-phosphaphenanthrene-10-oxide (about 41.73 grams, 0.193 moles) after back to normal pressure and stirred for 4 hours to obtain a second mixture.

The second mixture was subjected to vacuum distillation to recycle toluene therefrom and then dried and crumbled to give 163.29 grams of white powders (theoretical mass: 181.43 grams, yield: 90%), which contained 3.34% of phosphorus and remained unmelted at 250° C., i.e., had a melting point more than 250° C. Data of $^1$H-NMR spectrum (400 MHz, CDCl$_3$+d$_6$DMSO): δ8.2-8.1 (m), 7.9-7.79 (m), 7.59 (s), 7.4-7.2 (m), 7.13 (t, J=6.4 Hz), 6.9-6.8 (m), 6.97 (t, J=3.2 Hz), 5.47 (d, J=4.4 Hz) 8.2-8.1 (m), 7.9-7.79 (m), 7.59 (s), 7.4-7.2 (m), 7.13 (t, J=6.4 Hz), 6.9-6.8 (m), 6.97 (t, J=3.2 Hz), 5.47 (d, J=4.4 Hz). Data of $^{31}$P-NMR spectrum (202 MHz, CDCl$_3$+d$_6$DMSO): δ 30.97, 10.16, 9.75, 9.34. Data of FTIR spectrum: λ3392 (br.), 1643, 1542, 1446, 1366, 1276, 1147, 1097, 1063, 986, 962, 917, 836, 756 cm$^{-1}$. The analyzed and calculated ash contents were 37% and 23.61%, and [AA] % by titration and calculation were 66.87% and 52.91%.

The chemical structure of the white powders could be determined by the results of the foresaid analyses as follows:

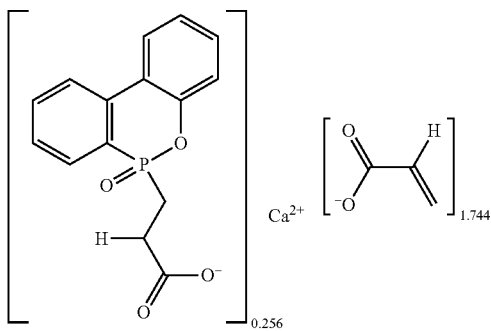

Comparative Example 1: Zinc Diacrylate (ZDA)

A 500 ml four-necked cylindrical shaped reaction flask equipped with a mechanical stirrer, a thermometer, a dropping funnel, and a Dean-Stark trap was charged with toluene (177 grams) and zinc oxide (45.00 grams, 0.553 moles), then slowly added with acrylic acid (81.6 grams, 1.133 moles, purchased from Formosa Plastics Corporation and contained 200±20 ppm of hydroquinone monomethylether) through the dropping funnel while heated to 50±5° C. and stirred at the temperature for 2 hours to obtain a mixture. The mixture was vacuum distilled to remove 9.95 grams of water and recycle toluene, and then continued drying until no mass variation was noted to give 107.4 grams (theoretical mass: 114.7 grams, yield: 93.6%) of white powders.

The white powders remained unmelted at 220° C. Data of $^1$H-NMR spectrum (400 MHz, CDCl$_3$+d$_6$DMSO): δ6.18 (2H, dd, J=17 Hz, J=2 Hz), 6.01 (2H, dd, J=17 Hz, J=10 Hz), 5.59 (2H, dd, J=10 Hz, J=2 Hz). Data of FTIR spectrum: λ3400 (br.), 1946, 1644, 1566, 1434, 1372, 1275, 1068, 981, 935, 910, 831, 711, 677, 610, 470, 411 cm$^{-1}$. The analyzed and calculated ash contents were 38.6% and 39.2%, and [AA] % by titration and calculation were 66.4% and 69.5%.

Comparative Example 2: Zinc Dimethacrylate (ZDMA)

The zinc dimethacrylate of Comparative Example 2 was mainly prepared by the method as described in Comparative Example 1, except that the acrylic acid of Comparative Example 1 was replaced by methacrylic acid in an amount of 97.0 grams (1.13 moles). Said methacrylic acid was purchased from Formosa Plastics Corporation and contained 250±20 ppm of hydroquinone monomethylether.

After drying and crumbling steps, 125.8 grams (theoretical mass: 130.3 grams, yield 96.5%) of white powders were obtained, which remained unmelted at 220° C. Data of $^1$H-NMR spectrum (400 MHz, CDCl$_3$+d$_6$DMSO): δ6.03 (2H, s), 5.38 (2H, s), 1.83 (6H, s). FTIR spectrum: λ2980, 1655, 1611, 1545, 1458, 1424, 1374, 1246, 1009, 945, 831, 624, 436 cm$^{-1}$. The analyzed and calculated ash contents were 31.9% and 34.6%, and [MAA] % by titration and calculation were 65.7% and 73.1%.

Comparative Example 3: Calcium Diacrylate (CDA)

A 500 ml four-necked cylindrical shaped reaction flask equipped with a mechanical stirrer, a thermometer, a dropping funnel, and a Dean-Stark trap was charged with toluene (177 grams) and calcium oxide (45 grams, 0.804 moles), then slowly added with acrylic acid (118.69 grams, 1.648 moles through the dropping funnel while heated to 50±5° C. and stirred at the temperature for 2 hours to obtain a mixture. The mixture was vacuum distilled to remove 14.47 grams of water and recycle toluene, and then continued drying until no mass variation was noted to give 116.39 grams (theoretical mass: 149.22 grams, yield: 78%) of white powders.

The white powders remained unmelted at 250° C. Data of $^1$H-NMR spectrum (400 MHz, CDCl$_3$+d$_6$DMSO): δ6.18-6.01 (m), 5.69-5.69 (m). Data of FTIR spectrum: λ3370 (br.), 1642, 1536, 1446, 1372, 1275, 1066, 986, 963, 919, 837 cm$^{-1}$. The analyzed and calculated ash contents were 29.87% and 30.78%, and [AA] % by titration and calculation were 68.24% and 79.1%.

Test Example 1

The metallic crosslinking coagents of Examples 1, 5, and 6 with zinc diacrylates of Comparative Example 1 and commercial product (trade name: K-CURE339, which contained 92 wt % of zinc diacrylate as effective component and 8 wt % of zinc stearate) were used as crosslinking coagents and a control sample without addition of crosslinking coagent was also prepared under same conditions for comparison, so as to verify the influence of metallic crosslinking coagents of the present invention and the zinc diacrylate in the prior art on the crosslinking efficiency and mechanical properties of the resin compositions.

The Brabender mixer (type: PL2100) was set at 70° C. with a screw speed of 100 rpm first. As listed in Table 1 below, the crosslinking coagent, polybutadiene rubber (trade name: Lanxess CB23), and zinc oxide were fed in the mixer and mixed for 1 minute, and then added with dicumyl peroxide (DCP) and further stirred for 1 minute to prepare resin compositions, each of the resin compositions weighed about 60 grams in total.

Said resin compositions were respectively cold pressed under room temperature, about 25° C. to 30° C., and 100 kgf/cm$^2$ for 10 minutes to form the resin films of samples 1 to 5 and of control sample 1. Each resin film was cut into three pieces, each weighed 5.5 grams, and then analyzed by a rheometer (model: EKT-2000S). Results were shown in FIG. 1, FIG. 2 and Table 1.

titration multiplied by the amount of the respective crosslinking coagent, contained in the resin compositions were also close to each other. As indicated in Table 1, the addition of metallic crosslinking coagent of Example 1, 5, or 6 increased the maximum torque and shortened the scorch time of the resin composition in comparison with the resin composition free of the crosslinking coagent. It showed that the metallic crosslinking coagent in accordance with the present invention is effective to improve the mechanical strength and crosslinking efficiency of the resin composition. The use of metallic crosslinking coagent of Example 1, 5, or 6 further shortened the curing time as required in comparison with the resin composition added with the zinc diacrylate of Comparative Example 1, commercial zinc diacrylate, or without any addition of crosslinking coagent. Accordingly, the metallic crosslinking coagent in accordance with the present invention is also useful to increase the curing rate of the resin composition.

Test Example 2

In the instant test example, the metallic crosslinking coagent of Example 1 and zinc diacrylate of Comparative Example 1 were used as crosslinking coagents, and a control

TABLE 1 the material of crosslinking coagents and amounts of the components contained in the resin compositions of samples 1 to 5 and control sample 1 and the results of the resin films made from the resin compositions of samples 1 to 5 and of control sample 1

|  | Control Sample 1 | Sample 1 | Sample 2 | Sample 3 | Sample 4 | Sample 5 |
| --- | --- | --- | --- | --- | --- | --- |
| Amount of polybutadiene rubber (phr) | 100 | 100 | 100 | 100 | 100 | 100 |
| Amount of zinc oxide (phr) | 5 | 5 | 5 | 5 | 5 | 5 |
| Amount of DCP (phr) | 0.12 | 0.12 | 0.12 | 0.12 | 0.12 | 0.12 |
| Sample No. of crosslinking coagent | N/A | Example 1 | Example 5 | Example 6 | Comparative Example 1 | Commercially available ZDA |
| Amount of crosslinking coagent (phr) | 0 | 13 | 16 | 16 | 10 | 10 |
| Minimum torque, ML (dN-m) | 1.18 | 1.40 | 1.25 | 1.18 | 1.38 | 1.23 |
| Maximum torque, MH (dN-m) | 7.46 | 14.94 | 14.36 | 15.78 | 17.36 | 19.59 |
| Scorch time, TS2 (sec) | 50 | 33 | 29 | 26 | 33 | 29 |
| Curing time, TC90 (sec) | 179 | 163 | 147 | 142 | 174 | 175 |

Figure 2:
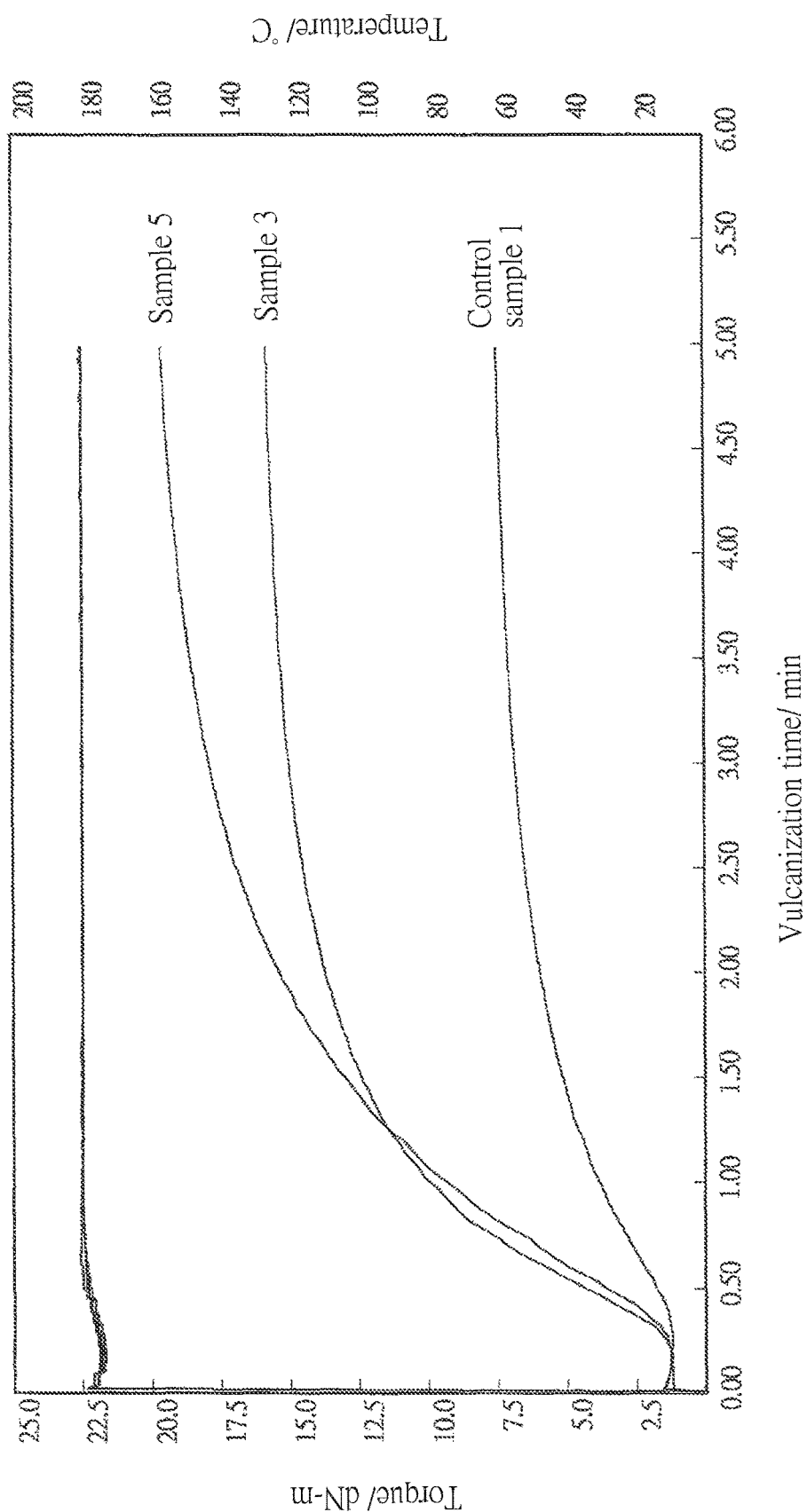
FIG. 2 is a graph showing the vulcanization curves of the resin composition comprising the metallic crosslinking coagent of Example 6 (Sample 3), of the resin composition comprising the commercial zinc diacrylate (Sample 5), and of the resin composition without adding any metallic crosslinking coagent (Control Sample 1).

With reference to FIG. 1, in comparison with the vulcanization curve of the control sample 1, the resin composition (sample 1) contained the metallic crosslinking coagent of Example 1, the resin composition (sample 2) contained the metallic crosslinking coagent of Example 5, and the resin composition (sample 4) contained zinc diacrylate of Comparative Example 1 were all vulcanized as desired. With reference to FIG. 2, both the resin composition (sample 3) contained the metallic crosslinking coagent of Example 6 and the resin composition (sample 5) contained commercial zinc diacrylate were vulcanized as desired.

As shown in the above Table 1, the amounts of polybutadiene rubber, zinc oxide, and DCP used in the control sample were respectively identical to those used in the samples 1 to 5 to ensure the reliability of the experimental results. The effective amounts of acrylate, i.e, the [AA] % by sample without any addition of crosslinking coagent was also prepared under same conditions for comparison.

The Brabender mixer as used in test example 1 was set at 70° C. with a screw speed of 100 rpm first. As listed in Table 2, the crosslinking coagent, ethylene propylene diene monomer rubber (EPDM, trade name: Nordel IP 4770R), and zinc oxide were fed in the mixer and mixed for 1 minute, and then added with DCP and further stirred for 1 minute to prepare resin compositions, each of the resin compositions weighed about 60 grams in total.

Said resin compositions were respectively cold pressed under room temperature, about 25° C. to 30° C., and 100 kgf/cm$^2$ for 10 minutes to form the resin films of samples 6 and 7 and control sample 2. Each resin film was cut into three pieces, each weighed 5.5 grams, and then analyzed by a rheometer (model: EKT-2000S). Results were shown in FIG. 3 and Table 2.

TABLE 2 the material of crosslinking coagents and amounts of the components contained in the resin compositions of samples 6 and 7 and control sample 2 and the results of the resin films made from the resin compositions of samples 6 and 7 and control sample 2

|  | Control Sample 2 | Sample 6 | Sample 7 |
|---|---|---|---|
| Amount of EPDM (phr) | 100 | 100 | 100 |
| Amount of zinc oxide (phr) | 5 | 5 | 5 |
| Amount of DCP (phr) | 2 | 2 | 2 |
| Sample No. of crosslinking coagent | N/A | Example 1 | Comparative Example 1 |
| Amount of crosslinking coagent (phr) | 0 | 13 | 10 |
| Minimum torque, ML (dN-m) | 1.95 | 2.47 | 2.47 |
| Maximum torque, MH (dN-m) | 19.51 | 25.43 | 27.91 |
| Scorch time, TS2 (sec) | 30 | 22 | 22 |
| Curing time, TC90 (sec) | 165 | 146 | 136 |

Figure 3:
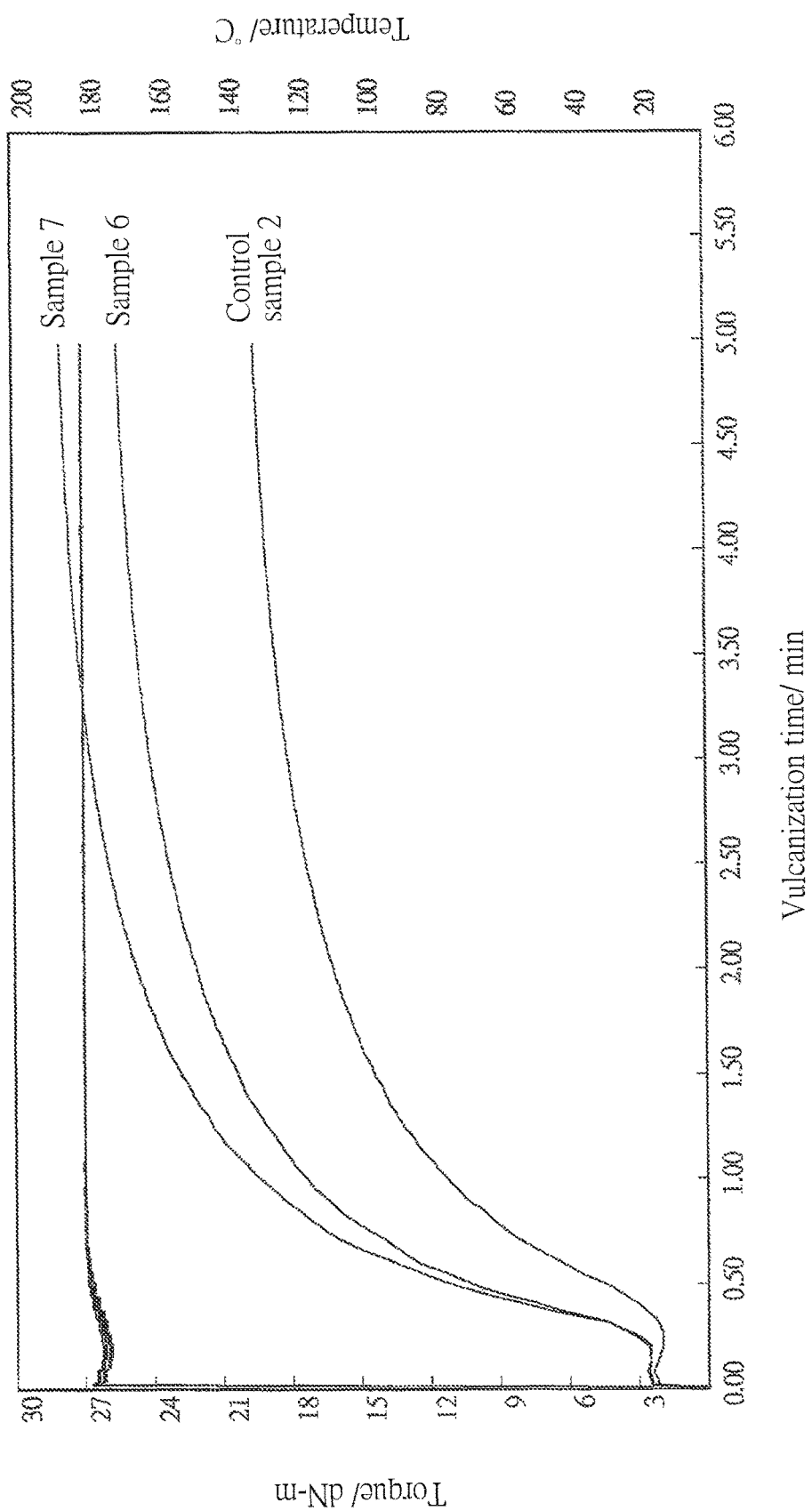
FIG. 3 is a graph showing the vulcanization curves of the resin composition comprising the metallic crosslinking coagent of Example 1 (Sample 6), of the resin composition comprising zinc diacrylate of Comparative Example 1 (Sample 7), and of the resin composition without adding any metallic crosslinking coagent (Control Sample 2).

With reference to FIG. 3, in comparison with the vulcanization curve of the control sample 2, both the resin composition (sample 6) contained the metallic crosslinking coagent of Example 1 and the resin composition (sample 7) contained zinc diacrylate of Comparative Example 1 were vulcanized as desired.

As shown in the above Table 2, the amounts of EPDM, zinc oxide, and DCP used in the control sample were respectively identical to those used in samples 6 and 7, and the effective amounts of acrylate, i.e, the [AA] % by titration multiplied by the amount of the respective crosslinking coagent, contained in the resin compositions were close to each other. According to the results in Table 2, the addition of metallic crosslinking coagent of Example 1 in the resin composition increased the maximum torque and shortened the scorch and curing time of the resin composition in comparison with the resin composition without adding any crosslinking coagent. Accordingly, the metallic crosslinking coagent in accordance with the present invention is also effective to improve the mechanical strength, crosslinking efficiency, and the curing rate of the resin composition.

Test Example 3

In the instant test example, the metallic crosslinking coagent of Example 1 and zinc diacrylate of Comparative Example 1 were used as crosslinking coagents, and a control sample without any addition of crosslinking coagent was also prepared under same conditions for comparison.

The Brabender mixer as used in test example 1 was set between 130° C. and 140° C. with a screw speed of 100 rpm before mixing. As listed in Table 3 below, low-density polyethylene (LDPE, trade name: LDPE LD100.BW purchased from ExxonMobile) and DCP were fed in the mixer and mixed for 3 minutes, and then added with crosslinking coagent and heated to 170° C. to 180° C. to undergo vulcanization for 6 minutes. After slowing down to 60 rpm to 80 rpm, the phosphorus-based flame retardant as listed in Table 3 were slowly added in the mixture and further stirred for 1 minute to observe the compatibility between the LDPE and the phosphorus-based flame retardant during the vulcanization. Results were shown in Table 3 below.

The phosphorus-based flame retardants added in the resin compositions of samples 8, 9, and 12 were KFR-DOPO (CAS No. 35948-25-5) purchased from Kuo Ching Chemical Co., Ltd., which contained 14.3% of phosphorus. In the resin compositions of samples 10, 11, and 13, the added phosphorus-based flame retardants were SPS-100 (CAS No. 260408-02-4) purchased from Otsuka Chemical Co., Ltd., which contained 13.4% of phosphorus.

TABLE 3 the material of crosslinking coagents and amounts of the components contained in the resin compositions of samples 8 to 13 and control sample 3, the total phosphorus content, and the compatibility during vulcanization

|  | Control Sample 3 | Sample 8 | Sample 9 | Sample 10 | Sample 11 | Sample 12 | Sample 13 |
|---|---|---|---|---|---|---|---|
| Amount of LDPE (phr) | 100 | 100 | 100 | 100 | 100 | 100 | 100 |
| Amount of DCP (phr) | 0.1 | 0.1 | 0.1 | 0.1 | 0.1 | 0.1 | 0.1 |
| Sample No. of crosslinking coagent | N/A | Example 1 | Example 1 | Example 1 | Example 1 | Comparative Example 1 | Comparative Example 1 |
| Amount of crosslinking coagent (phr) | 0 | 10 | 20 | 20 | 20 | 10 | 20 |
| Amount of KFR-DOPO (phr) | 15 | 15 | 15 | 0 | 0 | 15 | 0 |
| Amount of SPS-100 (phr) | 0 | 0 | 0 | 20 | 25 | 0 | 20 |
| Total phosphorus content (wt %) | <1.86 | 1.98 | 2.09 | 2.39 | 2.77 | <1.71 | <1.91 |
| Compatibility during vulcanization | Incompatible | Compatible | Compatible | Compatible | Compatible | Degradation | Degradation |

As shown in the above Table 3, the total phosphorus content was calculated by dividing the sum of the product of the amount of the crosslinking coagent and its phosphorus content added with the product of the amount of the phosphorus-based flame retardant and its phosphorus content by the total amount of every component in the resin composition.

In comparison with the results of compatibility of samples 12 and 13 and control sample 3, the addition of metallic crosslinking coagent of Example 1 in the resin composition not only overcame the problems of incompatibility between LDPE and the phosphorus-based flame retardant including KFR-DOPO or SPS-100 and chalking, and also improved the total amount of the phosphorus contained in the resin composition. Accordingly, the metallic crosslinking coagent in accordance with the present invention is further beneficial to develop a safe and environmentally friendly flame-retardant material.

Test Example 4

In the instant test example, the metallic crosslinking coagent of Example 2 and zinc diacrylate of Comparative Example 1 were used as crosslinking coagents. Before mixing, the Brabender mixer as used in test example 1 was set at 70° C. with a screw speed of 100 rpm. As listed in Table 4, the crosslinking coagent, EPDM (trade name: Nordel IP 4770R) were mixed and stirred for 1 minute in the mixer, and then added with DCP and further stirred for 1 minute to prepare resin compositions, each of the resin compositions weighed about 60 grams in total.

Said resin compositions were respectively cold pressed under room temperature and 100 kgf/cm$^2$ for 10 minutes to form the resin films. Each resin film was cut into 7 grams of pieces for testing.

After that, each test piece was placed into a mold with a size of 12 cm×12 cm×2 mm, and then molded by hot pressing machine (model: ST-7613) under 170° C. and 5 kgf/cm$^2$ for 3 minutes and then 170° C. and 100 kgf/cm$^2$ for 10 minutes. After cooling to room temperature, the test piece was further pressed under and 100 kgf/cm$^2$ for 10 minutes to obtain the hot pressed test piece.

Each hot pressed test piece was cut into strips with the same weight, as original weight of the test sheet before adsorption (W0). The strip was immersed in the phosphorus-based flame retardant (REOFOS 95 purchased from Chemtura Corp., CAS No. 68937-41-7, which contained 7.6% of phosphorus) and then placed in a heat-circulation oven set at 50° C. for 24 hours. The excess water on the surface of the strip was wiped off and weighed to record the weight of the test sheet after adsorption (W1). The weight change of the test sheet before and after adsorption, the adsorption amount, and phosphorus content were listed in Table 4. The adsorption amount (%) was calculated from dividing the difference of the weights of test sheet before and after adsorption by the weight of test sheet before adsorption

TABLE 4 the material of crosslinking coagents and amounts of the components contained in the resin compositions of samples 14 to 19 and the adsorption results of the test sheets made from the resin composition of samples 14 to 19

| | Sample 14 | Sample 15 | Sample 16 | Sample 17 | Sample 18 | Sample 19 |
|---|---|---|---|---|---|---|
| Amount of EPDM (phr) | 100 | 100 | 100 | 100 | 100 | 100 |
| Amount of DCP (phr) | 2.00 | 2.00 | 2.00 | 2.00 | 2.00 | 2.00 |
| Sample No. of crosslinking coagent | Example 2 | | | Comparative Example 1 | | |
| Amount of crosslinking coagent (phr) | 5.37 | 11.3 | 18.0 | 5.37 | 11.3 | 18.0 |
| Weight of the test sheet before adsorption (grams) | 4.74 | 4.67 | 4.80 | 4.54 | 4.74 | 4.61 |
| Weight of the test sheet after adsorption (grams) | 5.18 | 5.19 | 5.32 | 4.93 | 5.18 | 5.07 |
| Adsorption amount of REOFOS 95 (%) | 9.28 | 11.13 | 10.83 | 8.59 | 9.28 | 9.00 |
| Phosphorus content before adsorption (wt %) | 0.32 | 0.68 | 1.00 | 0 | 0 | 0 |
| Phosphorus content after adsorption (wt %) | 0.94 | 1.37 | 1.64 | 0.38 | 0.64 | 0.69 |

As shown in Table 4, except the different chemical structures of the metallic crosslinking coagents between samples 14 to 16 and samples 17 to 19, the amounts of EPDM and DCP were respectively identical among samples 14 to 19, the amount of metallic crosslinking coagent used in sample 14 was identical to that of sample 17, the amount of metallic crosslinking coagent used in sample 15 was also identical to that of sample 18, and the amount of metallic crosslinking coagent used in sample 16 was identical to that of sample 19, so as to ensure the reliability of the experimental results.

From the results of adsorption of the phosphorus-based flame retardants between samples 14 and 17, between samples 15 and 18, and between samples 16 and 19, the metallic crosslinking coagent of Example 2 improved the compatibility between EPDM and REOFOS 95, such that the resin composition added with the metallic crosslinking coagent enabled the resin film made therefrom to adsorb more amount of the phosphorus-based flame retardant and increase the total phosphorus content of material, and thus improve the flame retardancy of the material.

Test Example 5

In the instant test example, the metallic crosslinking coagents of Example 3, 5, and 8 and zinc diacrylate of Comparative Example 1 were used as crosslinking coagents. Before mixing, the Brabender mixer as used in test example 1 was set at 70° C. with a screw speed of 100 rpm. As listed in Table 5, the crosslinking coagent and EPDM (trade name: Nordel IP 4770R) were mixed and stirred for 1 minute in the mixer, and added with DCP and further stirred for 1 minute to prepare resin compositions, each of the resin compositions weighed about 60 grams in total.

Said resin compositions were respectively cold pressed under room temperature and 100 kgf/cm$^2$ for 10 minutes to form the resin films. Each resin film was cut into 7 grams of pieces for testing.

Each test piece was placed into a mold with a size of 12 cm×12 cm×2 mm, and then molded by hot pressing machine (model: ST-7613) under 170° C. and 5 kgf/cm² for 3 minutes and then 170° C. and 100 kgf/cm² for 10 minutes. After cooling to room temperature, the test piece was further pressed under 100 kgf/cm² for 10 minutes to obtain the hot pressed test piece.

The hot pressed test piece was cut into strips with the same weight, as original weight of the test sheet before adsorption (W0). The strip was immersed in the phosphorus-based flame retardant (SPC-100 purchased from Otsuka Chemical Co., Ltd., CAS No. 1203477-21-7, which contained 12.6% of phosphorus) and then placed in a heat-circulation oven set at 50° C. for 24 hours. The excess water on the surface of the strip was wiped off and weighed to record the weight of the test sheet after adsorption (W1). The weight change of each test sheet before and after adsorption, the adsorption amount, and phosphorus content were listed in Table 5. The adsorption amount (%) was calculated from dividing the difference of the test sheet before and after adsorption by the weight of test sheet before adsorption.

TABLE 5 the material of crosslinking coagents and amounts of the components in the resin compositions of samples 20 to 23 and the adsorption results of the test sheets made from the resin composition of samples 20 to 23

|  | Sample 20 | Sample 21 | Sample 22 | Sample 23 |
|---|---|---|---|---|
| Amount of EPDM (phr) | 100 | 100 | 100 | 100 |
| Amount of DCP (phr) | 2.00 | 2.00 | 2.00 | 2.00 |
| Sample No. of crosslinking coagent | Example 3 | Example 5 | Example 8 | Comparative Example 1 |
| Amount of crosslinking coagent (phr) | 11.3 | 11.3 | 11.3 | 11.3 |
| Weight of the test sheet before adsorption (grams) | 7.09 | 6.41 | 6.76 | 7.57 |
| Weight of the test sheet after adsorption (grams) | 7.77 | 7.00 | 7.23 | 8.14 |
| Adsorption amount of SPC-100 (%) | 9.59 | 9.20 | 6.95 | 7.53 |
| Phosphorus content before adsorption (wt %) | 0.33 | 0.34 | 0.82 | 0 |
| Total phosphorus content of the test sheet (wt %) | 1.40 | 1.37 | 1.58 | 0.88 |

As shown in Table 5, to ensure the reliability of the experimental results, the amounts of EPDM and DCP were respectively identical among samples 20 to 23, and the amounts of metallic crosslinking coagents used in sample 20 to 23 were identical to each other. The only difference between samples 20 to 23 was the chemical structure of the metallic crosslinking coagent.

From the results of adsorption of phosphorus-based flame retardant among samples 20 to 23, the metallic crosslinking coagent of any one of Examples 3, 5, and 8 did provide a better compatibility between EPDM and SPC-100 in comparison with the zinc diacrylate of Comparative Example 1. The resin film made from the resin composition contained such a metallic crosslinking coagent could adsorb more amount of phosphazene compound, thus increasing the phosphorus content of the test sheet. It demonstrated that the metallic crosslinking coagent in accordance with the present invention did improve the flame retardancy of the resin film because of the more phosphorus-containing structure. The nitrogen and phosphorus material was decomposed into more thermally stable crosslinked products induced the test sheet being apt to be carbonized under heat, thereby improving the flame retardancy of the test sheet.

Test Example 6

In the instant test example, the metallic crosslinking coagents of Example 4 and 7 and zinc dimethacrylate of Comparative Example 2 were used as crosslinking coagents. Samples 24 to 26 with the composition as listed in Table 6 below were prepared by the method as described in test example 5. The strips for adsorption analyses were also prepared by the method as described in test example 5. Results of the weight change of each test sheet before and after adsorption, the adsorption amount, and phosphorus content were listed in Table 6.

TABLE 6 the material of crosslinking coagents and amounts of the components in the resin compositions of samples 24 to 26 and the adsorption results of the test sheets made from the resin composition of samples 24 to 26

|  | Sample 24 | Sample 25 | Sample 26 |
|---|---|---|---|
| Amount of EPDM (phr) | 100 | 100 | 100 |
| Amount of DCP (phr) | 2.00 | 2.00 | 2.00 |
| Sample No. of crosslinking coagent | Example 4 | Example 7 | Comparative Example 2 |
| Amount of crosslinking coagent (phr) | 11.3 | 11.3 | 11.3 |
| Weight of the test sheet before adsorption (grams) | 7.11 | 7.09 | 7.41 |
| Weight of the test sheet after adsorption (grams) | 7.62 | 7.53 | 7.86 |
| Adsorption amount of SPC-100 (%) | 7.17 | 6.21 | 6.07 |
| Phosphorus content before adsorption (wt %) | 0.50 | 0.33 | 0 |
| Total phosphorus content of the test sheet (wt %) | 1.31 | 1.05 | 0.72 |

As shown in Table 6, to ensure the reliability of the experimental results, the amounts of EPDM and DCP were respectively identical among samples 24 to 26, and the amounts of metallic crosslinking coagents used in sample 24 to 26 were identical to each other. The only difference between samples 24 to 26 was the chemical structure of the metallic crosslinking coagent.

As indicated by the results of test example 5, the results of Table 6 showed that the metallic crosslinking coagent of Example 4 or 7 also provided a better compatibility between EPDM and SPC-100 in comparison with the zinc dimethacrylate of Comparative Example 2. The resin film made from the resin composition contained such a metallic crosslinking coagent could adsorb more amount of phosphazene compound, thus increasing the phosphorus content of the test sheet and improving the flame retardancy by the phosphorus-containing structure.

Test Example 7

In the instant test example, the metallic crosslinking coagent of Example 10 and calcium diacrylate of Comparative Example 3 were used as crosslinking coagents.

The Brabender mixer as used in test example 1 was set between 130° C. and 140° C. with a screw speed of 100 rpm before mixing. As listed in Table 7 below, low-density polyethylene (LDPE, trade name: LDPE LD100.BW purchased from ExxonMobile) and DCP were fed in the mixer and mixed for 3 minutes, and then added with crosslinking coagent and heated to 170° C. to 180° C. to undergo vulcanization for 6 minutes. After slowing down to 60 rpm to 80 rpm, the phosphorus-based flame retardant as listed in Table 7 were slowly added in the mixture and further stirred for 1 minute to observe the compatibility between the LDPE and the phosphorus-based flame retardant during the vulcanization. Results were shown in Table 7 below.

The phosphorus-based flame retardants added in the resin compositions of samples 27 and 29 were KFR-DOPO (CAS No. 35948-25-5) purchased from Kuo Ching Chemical Co., Ltd., which contained 14.3% of phosphorus. In the resin compositions of samples 28 and 30, the added phosphorus-based flame retardants were SPS-100 (CAS No. 260408-02-4) purchased from Otsuka Chemical Co., Ltd., which contained 13.4% of phosphorus.

TABLE 7 the material of crosslinking coagents and amounts of the components contained in the resin compositions of samples 27 to 30, the total phosphorus content, and the compatibility during vulcanization

| | Sample 27 | Sample 28 | Sample 29 | Sample 30 |
|---|---|---|---|---|
| Amount of LDPE (phr) | 100 | 100 | 100 | 100 |
| Amount of DCP (phr) | 0.1 | 0.1 | 0.1 | 0.1 |
| Sample No. of crosslinking coagent | Example 10 | | Comparative Example 3 | |
| Amount of crosslinking coagent (phr) | 20 | 20 | 20 | 20 |
| Amount of KFR-DOPO (phr) | 15 | 0 | 15 | 0 |
| Amount of SPS-100 (phr) | 0 | 20 | 0 | 20 |
| Total phosphorus content (wt %) | 2.09 | 2.39 | <1.71 | <1.91 |
| Compatibility during vulcanization | Compatible | Compatible | Partially Compatible | Partially Compatible |

As shown in the above Table 7, the total phosphorus content was calculated by dividing the sum of the product of the amount of the crosslinking coagent and its phosphorus content added with the product of the amount of the phosphorus-based flame retardant and its phosphorus content by the total amount of every component in the resin composition.

In comparison with the results of samples 27 and 29, the addition of metallic crosslinking coagent of Example 10 in the resin composition not only improved the compatibility between LDPE and the phosphorus-based flame retardant including KFR-DOPO, and also increased the total amount of the phosphorus contained in the resin composition. The similar effects could be obtained from the results of samples 28 and 30. Like aforementioned metallic crosslinking coagents of the present invention, the metallic crosslinking coagent of $Ca^{2+}$ is also beneficial to develop a safe and environmentally friendly flame-retardant material.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A metallic crosslinking coagent, having a chemical structure represented by the following formula (I):

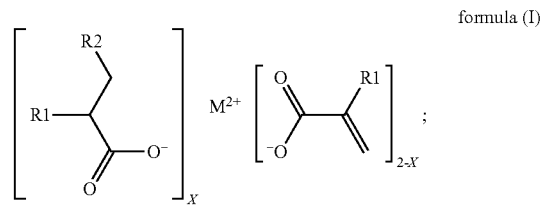

formula (I)

wherein in the above formula (I),
$M^{2+}$ is a divalent metal ion;
R1 is hydrogen or an alkyl group;
R2 is

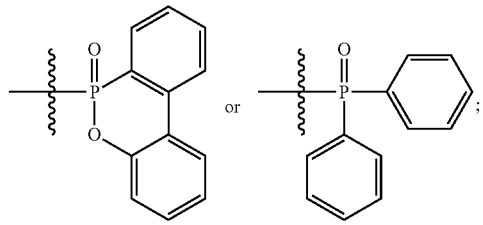 [SMILES: *P1(=O)Oc2ccccc2-c2ccccc21 ; *P(=O)(c1ccccc1)c1ccccc1]

and
X is larger than 0 and less than 2.

2. The metallic crosslinking coagent as claimed in claim 1, wherein $M^{2+}$ is zinc ion, magnesium ion, calcium ion, or barium ion.

3. The metallic crosslinking coagent as claimed in claim 1, wherein X is larger than 0 and less than 1.

4. The metallic crosslinking coagent as claimed in claim 1, wherein the alkyl group is a saturated alkyl group having 1 to 6 carbon atoms.

5. A resin composition comprising a polymer and the metallic crosslinking coagent as claimed in claim 1.

6. The resin composition as claimed in claim 5, wherein the amount of the metallic crosslinking coagent ranges from 10 parts by weight to 900 parts by weight per 100 parts by weight of the polymer.

7. The resin composition as claimed in claim 5, wherein the resin composition comprises an organic peroxide, the polymer is a vulcanizable polymer, and the amount of the metallic crosslinking coagent ranges from 5 parts by weight to 40 parts and the amount of the organic peroxide ranges from 0.1 parts by weight to 3 parts by weight per 100 parts by weight of the polymer.

8. The resin composition as claimed in claim 7, wherein the vulcanizable polymer is selected from the group consisting of: polyolefin, ethylene-α-olefin copolymer, ethylene-α-olefin-nonconjugated diene copolymer, polyethylene, ethylene propylene rubber, ethylene propylene diene monomer rubber, polybutadiene rubber, polyisobutylene rubber, natural rubber, polyisoprene rubber, styrene-butadiene-styrene block copolymer, styrene-isoprene-styrene block copolymer, styrene butadiene rubber, partially-hydrogenated styrene-butadiene-styrene block copolymer, nitrile rubber, polyolefin elastomer, and combinations thereof.

9. The resin composition as claimed in claim 7, wherein the organic peroxide is selected from the group consisting of: alkyl hydroperoxide, dialkyl hydroperoxide, peroxyester, diperoxyketal, diacyl peroxide, peroxydicarbonates, and combinations thereof.

10. The resin composition as claimed in claim 5, wherein the resin composition comprises a halogen-free flame retardant selected from the group consisting of an organic phosphorus-based flame retardant, an inorganic flame retardant, and a combination thereof, wherein a total amount of the halogen-free flame retardant ranges from 10 parts by weight to 200 parts by weight per 100 parts by weight of the polymer.

11. The resin composition as claimed in claim 5, wherein the resin composition comprises an organic phosphorus-based flame retardant, and the amount of the organic phosphorus-based flame retardant ranges from 10 parts by weight to 40 parts by weight per 100 parts by weight of the polymer.

12. A method of producing the metallic crosslinking coagent as claimed in claim 1, comprising steps of:
reacting an unsaturated carboxylic acid and a divalent metal oxide in a nonpolar solvent to form a first mixture;
mixing an organic phosphorus compound and the first mixture to form a second mixture;
collecting the metallic crosslinking coagent from the second mixture by purification.

13. The method as claimed in claim 12, wherein the unsaturated carboxylic acid is acrylic acid or methacrylic acid, the divalent metal oxide is zinc oxide, magnesium oxide, calcium oxide, barium oxide, zinc hydroxide, magnesium hydroxide, calcium hydroxide, or barium hydroxide, and the organic phosphorus compound is 9,10-dihydro-9-oxa-10-phosphaphenanthrene-10-oxide or diphenylphosphine oxide.

14. The method as claimed in claim 12, wherein a molar ratio of the unsaturated carboxylic acid to the divalent metal oxide ranges from 1.4:1 to 2.1:1, and a molar ratio of the divalent metal oxide to the organic phosphorus compound ranges from 1:0.05 to 1:2.

15. The method as claimed in claim 12, wherein the nonpolar solvent includes benzene, toluene, xylene, cyclohexane, hexane, heptane, octane, or any combinations thereof.

16. The method as claimed in claim 12, wherein the unsaturated carboxylic acid is reacted with the divalent metal oxide at a temperature ranging from 30° C. to 100° C., and the organic phosphorus oxide is mixed with the first mixture at a temperature ranging from 30° C. to 100° C.

17. The method as claimed in claim 12, wherein the method comprises reacting the unsaturated carboxylic acid, the divalent metal oxide, and an additive in the nonpolar solvent to form the first mixture, and the additive comprises a surfactant, an antioxidant, a polymerization inhibitor, or a lubricant.

18. A method of producing the metallic crosslinking coagent as claimed in claim 1, comprising steps of:
reacting an unsaturated metal carboxylate and an organic phosphorus compound in a nonaqueous solvent to form a third mixture; and
collecting the metallic crosslinking coagent from the third mixture by purification.

19. The method as claimed in claim 18, wherein the nonaqueous solvent has a water content less than 2%, and the nonaqueous solvent includes benzene, toluene, xylene, cyclohexane, hexane, heptane, octane, or any combinations thereof.

20. The method as claimed in claim 18, wherein the unsaturated metal carboxylate is zinc diacrylate, zinc dimethacrylate, magnesium diacrylate, magnesium dimethacrylate, calcium diacrylate, calcium dimethacrylate, barium diacrylate, or barium dimethacrylate, and the organic phosphorus compound is 9,10-dihydro-9-oxa-10-phosphaphenanthrene-10-oxide or diphenylphosphine oxide.

21. The method as claimed in claim 18, wherein a molar ratio of the unsaturated metal carboxylate to the organic phosphorus compound ranges from 1:0.05 to 1:2.

22. The method as claimed in claim 18, wherein the unsaturated metal carboxylate is reacted with the organic phosphorus oxide at a temperature ranging from 30° C. to 100° C.

23. The method as claimed in claim 18, wherein the method comprises mixing the unsaturated metal carboxylate, the organic phosphorus compound, and an additive in the nonaqueous solvent to form the third mixture, and the additive comprises a surfactant, an antioxidant, a polymerization inhibitor, or a lubricant.

* * * * *